United States Patent [19]

Inanaga et al.

[11] Patent Number: 5,276,740
[45] Date of Patent: Jan. 4, 1994

[54] EARPHONE DEVICE

[75] Inventors: Kiyofumi Inanaga; Hiroyuki Sogawa, both of Kanagawa; Yasuhiro Iida, Tokyo; Akira Kimura, Kanagawa, all of Japan

[73] Assignee: Sony Corporation, Tokyo, Japan

[21] Appl. No.: 18,468

[22] Filed: Feb. 16, 1993

Related U.S. Application Data

[63] Continuation of Ser. No. 762,028, Sep. 17, 1991, abandoned.

[30] Foreign Application Priority Data

Jan. 19, 1990 [JP] Japan ......................... 2-8509
Jan. 19, 1990 [JP] Japan ......................... 2-8510

[51] Int. Cl.$^5$ .............................. H04R 1/10
[52] U.S. Cl. .............................. 381/187; 381/25; 381/71; 381/72; 381/183
[58] Field of Search ............. 381/183, 187, 25, 71, 381/72

[56] References Cited

U.S. PATENT DOCUMENTS

| | | | |
|---|---|---|---|
| 4,173,715 | 11/1979 | Gosman | 381/19 |
| 4,455,675 | 6/1984 | Bose et al. | 381/96 |
| 4,833,719 | 5/1989 | Carme et al. | 381/94 |
| 4,864,610 | 9/1989 | Stevens | 381/187 |
| 4,972,492 | 11/1990 | Tanaka et al. | 381/187 |
| 5,001,763 | 3/1991 | Moseley | 381/71 |
| 5,022,486 | 6/1991 | Miura et al. | 381/187 |

FOREIGN PATENT DOCUMENTS

WO8900746 1/1989 PCT Int'l Appl. .

Primary Examiner—John K. Peng
Assistant Examiner—Edward Lefkowitz
Attorney, Agent, or Firm—Lewis H. Eslinger; Jay H. Maioli

[57] ABSTRACT

An earphone device includes an acoustic tube having an inner diameter substantially identical to that of the external auditory canal has an ear mounting portion at one end and an acoustic non-reflecting portion at the outer end. An earphone unit and an internal microphone unit are mounted on the periphery of the acoustic tube adjacent each other and communicate with the interior of the acoustic tube with their respective vibration plates facing inwardly of the tube. The phase of the signal representing the external noise in the acoustic tube picked up by the internal microphone unit is reversed and combined with the audio signal fed to the earphone unit. The earphone device also includes an external microphone unit on the outside of the acoustic tube and a variable ratio mixing circuit for mixing the input audio program signal, the reversed phase signal obtained from the internal microphone unit, and the signal from the external microphone unit, so that external sounds can be heard without removing the earphone device.

5 Claims, 4 Drawing Sheets

EARPHONE DEVICE

This is a continuation of application Ser. No. 07/762,028, filed Sep. 17, 1991 now abandoned.

TECHNICAL FIELD

The present invention relates to a so-called active type earphone device which is capable of reducing external noises.

BACKGROUND TECHNIQUE

So-called ear fitting type noise reducing apparatus which is used in working in an environment in which external noises are very loud has been widely known. This ear fitting type noise reducing apparatus is worn in such a manner that the headphone cap covers the ears for reducing the external noises. The headphone cap is pressed upon the temple of the head so that external noises from the environment will not pass through a gap between the temple of the head and the headphone cap. The noise reducing apparatus has been used in such a manner.

However, it is necessary to strongly press the headphone cap of the above mentioned prior art noise reducing apparatus upon the temple of the head in order to prevent external noises from the environment from entering the gap between the headphone cap and the temple of the head. Accordingly, an oppressive sensation is felt on the temple of the head and the noise reducing apparatus per se is large in size and heavy. Therefore, use of this apparatus for a long period of time is unbearable. Also a headphone cap cannot shield noise having low frequencies (several hundred Hz to not higher than 1 KHz). If noises are reduced by the above mentioned method and reproduced sounds are attempted to be listened to, an effect of so-called localization in head occurs due to reflections of the reproduced sound in the headphone cap so that an adverse influence is given to communication, etc. The effect of localization in head occurs as follows: Reflections occur between the headcap and the entrance of the external auditory canal since the acoustic impedance in the entrance of the external auditory canal is different from the impedance in the external auditory canal. The reflected wave returns to the ear drum, resulting in that a sound image is localized in the head. An uncomfortable feeling as if the ear were plugged is felt.

So-called active type earphone devices have been known as earphone devices used in working in loud noise places. Such type earphone devices reduce the noises generated near the headphone unit by converting the external noises into electrical signals by a microphone unit and by negatively feeding back the converted electrical signal in an opposite phase via a negative feed back loop.

Such active type earphone device has a high sound shielding ability and is thus capable of almost shielding external sounds. Accordingly, it is very inconvenient for the user to remove the earphone device from the ear each time when the user desires to listen to external sounds such as emergency information or human voices.

The present invention was made under such circumstance.

It is an object of the present invention to provide an earphone device which will not cause an effect of localization in head and can be used for a long period of time without pressing the head and is capable of effectively reducing external noises.

It is another object of the present invention to provide an earphone device within which external sound can be listened to even if the earphone device which has been worn is not removed.

DISCLOSURE OF THE INVENTION

An earphone device of the present invention comprises an acoustic tube having an inner diameter which is substantially identical with that of the external auditory canal and is provided with an ear mounting portion at one end thereof and with an acoustic non-reflecting terminal at the other end thereof; and an earphone unit and an internal microphone unit which are disposed in the vicinity of the ear when the device is worn and are mounted on the periphery of the acoustic tube in adjacent relationship with each other so that vibration plates of the units face inwardly of the tube, whereby a signal obtained by the inner microphone unit, the phase of which has been reversed is supplied to the earphone unit for reducing the external noises. In the earphones device of the present invention, external noises are effectively reduced without pressing the temple of the head and uncomfortable feeling such as oppression is not felt even if the earphone device is used for a long period of time.

Another embodiment of the earphone device of the present invention comprises an acoustic tube having an inner diameter which is substantially identical with that of the external auditory canal and is provided with an ear mounting portion at one end thereof and with an acoustic non-reflecting terminal at the other end thereof; an external microphone unit disposed externally of said acoustic tube for converting the external sound into an electrical signal; an earphone unit and an internal microphone unit which are mounted on the periphery of the acoustic tube in adjacent relationship with each other so that vibration plates of the units face inwardly of the tube; and mixing ratio variable means for mixing the input audio signal, the signal obtained by negatively feeding back the signal obtained from said internal microphone unit and the signal obtained from the external microphone unit with each other at a desired ratio, the output signal of said mixing means being supplied to said earphone unit. In the earphone device of the present invention, external sounds can be listened to while the device is worn on the head and external noises which reach the ear can be reduced.

BEST MODES FOR EMBODYING THE INVENTION

Embodiments of the earphone of the present invention will be described with reference to the drawings.

Figure 1:
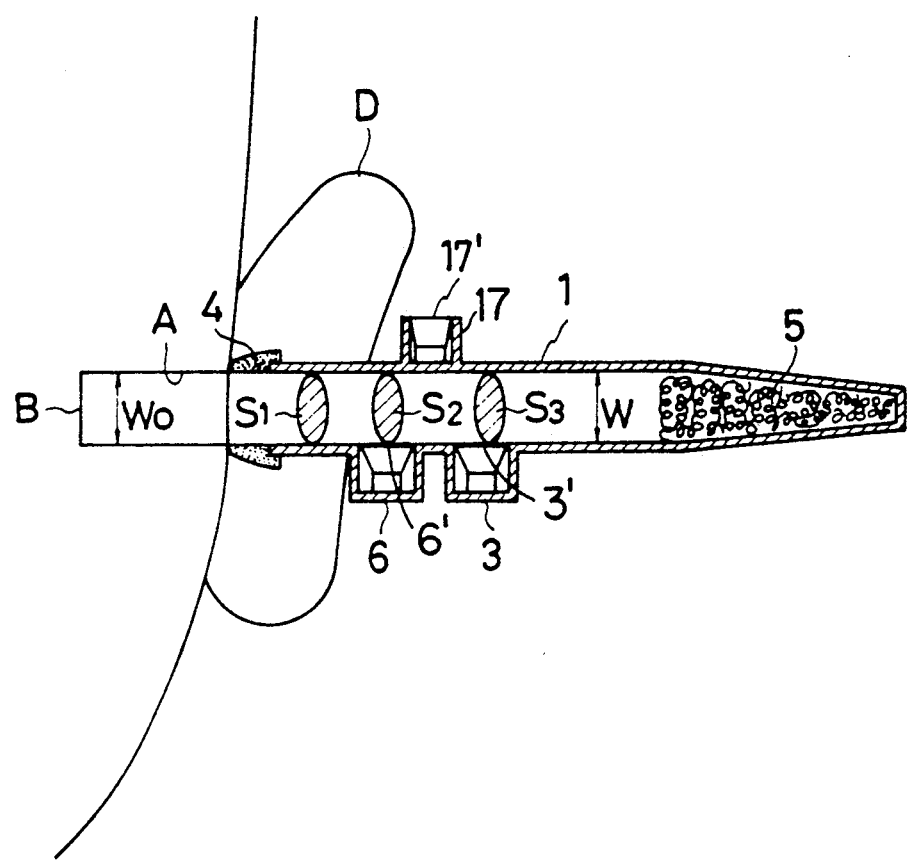
FIG. 1 is a sectional view of a part of an acoustic tube of an earphone device of the present invention.

FIG. 1 is a sectional view of an earphone device of the present invention.

In FIG. 1, the earphone device comprises an acoustic tube 1 having an inner diameter W which is substantially identical with the inner diameter $W_0$ of the external auditory canal A and which is provided with auricle mounting member 4 made of a material such as synthetic resin or rubber having an elasticity at one end thereof and with a sound absorbing member 5 such as felt at the other end thereof so that the other end becomes an acoustic non-reflection terminal, an earphone unit 3 and an internal microphone unit 6 adjacent to the earphone unit 3 provided on the periphery of the acoustic tube 1, each having a vibration plate 3' and 6' respectively facing inward of the tube.

The acoustic tube 1 forms an earphone casing. The inner diameter W is made uniform and substantially identical with the inner diameter $W_0$ of the external auditory canal A and the sound absorbing member 5 is provided at the other end to provide the acoustic non-reflecting terminal so that the acoustic impedance of the acoustic tube 1 is made substantially identical with the impedance of the external auditory canal A. So called localization in head is thus prevented. In order to prevent a change in the acoustic impedance, the earphone unit 3 and the inner microphone unit 6 are mounted on the side of the acoustic tube 1 so that the respective vibration plates or diaphragms 3' and 6' are parallel and flush with the inside of the tube 1, and the sectional area $S_1$ of the acoustic tube 1 is equal to the respective sectional areas $S_2$ and $S_3$ of the mounting portions of the earphone unit 3 and the microphone unit 6.

Figure 2:
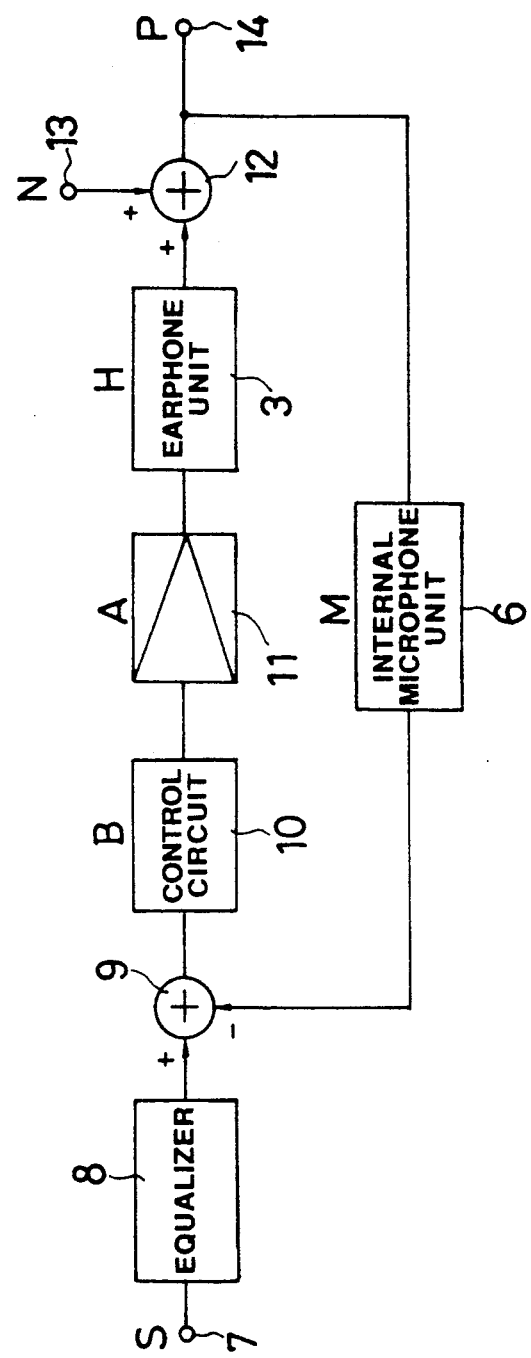
FIG. 2 is a block diagram showing the structure of the earphone device.

FIG. 2 is a block diagram showing the structure of the earphone device.

In this earphone device, a received signal is supplied to an equalizer 8 via an input terminal 7 as an input audio signal as shown in FIG. 2.

The equalizer 8 puts an emphasis upon the sound components in the input audio signal by increasing the amplification in an intermediate range of the frequency of the input audio signal. The output signal is supplied to a control circuit 10 via an adder 9 which will be described hereafter. Adjustment of the frequency in the equalizer 8 may be achieved by a desired level by adjustment.

The control circuit 10 controls the frequency characteristics of an input signal supplied from the adder 9 so that frequency characteristics of the whole circuit from the equalizer 8 to the earphone unit 3 corresponds to the audio frequency characteristics until the external noises reaches the ear.

An output signal from the control circuit 10 is supplied to the earphone unit 3 via an amplifier 11. The amplifier may change its amplification factor in order to make it easier to listen to reproduced sounds.

The earphone unit 3 provides a reproduced sound by electro-acoustically converting the output signal supplied from the amplifier 11.

The adder 12 adds the reproduced sound reaching the external auditory canal A after being provided from the earphone unit 3 with external noises supplied from the input terminal 13, that is, the external noises reaching the external auditory canal A via the earphone unit 3 and the acoustic tube 1 and external noises reaching the external auditory canal A through a gap between the earphone unit 3 and the ear. The adder 12 represents this operation in equivalent block diagram form. The reproduced sound which has been added with the external noises is picked up by the internal microphone 6 and is converted into an electrical signal. The internal microphone unit 6 reverses the phase of the electrical signal representative of the picked-up reproduced sound for supplying the same to the adder 9.

The adder 9 adds a signal having reversed phase supplied from the internal microphone unit 6 with the output signal from the equalizer 8.

This enables the sound provided from the earphone unit 3 to become a clear reproduced sound from which external noises are removed.

The reproduced sound is outputted via the output terminal 14.

If the level of the signal supplied from the input terminal 7, the transfer functions of the internal microphone unit 6, of the control circuit 10, of the amplifier circuit 11, and of the earphone unit 3, the level of the external noises supplied from the input terminal 14 and the level of the reproduced sound output from the output terminal 14 are represented as S, M, $\beta$, A, H, N and P, respectively, the level P of the reproduced sound is represented as follows:

$$P = \frac{AHM\beta}{1 + AHM\beta} S + \frac{1}{1 + AHM\beta} N$$

The transfer functions M, $\beta$, A and H are represented in frequency domain. If $AHM\beta >> 1$ at this time, the level P of the reproduced sound is represented as follows:

$$P = S + \frac{1}{AHM\beta} N$$

It is found from the above equation that the level P of the reproduced sound does not depend on the transfer functions A and B of the amplifier circuit 11 and the earphone unit 3 if the condition $AHM\beta >> 1$ is satisfied. Accordingly, the level of the external noise which has been negatively fed back by the internal microphone unit 6 independently of the level of the reproduced sound by changing the gain of the amplifier 11 under a condition $AHM\beta >> 1$. The effect of localization in head can be effectively prevented so that the reproduced sound can be clearly listened to by increasing the gain of the amplifier circuit 11 to increase the reduction amount of noise when the external noise is loud and by decreasing the gain of the amplifier circuit 11 when the external noise is less loud.

There is the possibility that the external sound can never be listened to if the noise reduction amount is increased by increasing the gain of the amplifier circuit 11. In order to enable the external sound to be listened to, an external microphone 17 for picking up external sounds may be provided externally of the acoustic tube 1. The signal of the external sound provided by the external microphone 17 may be supplied to the adder 9 in which it is added with the input audio signal.

Figure 3:
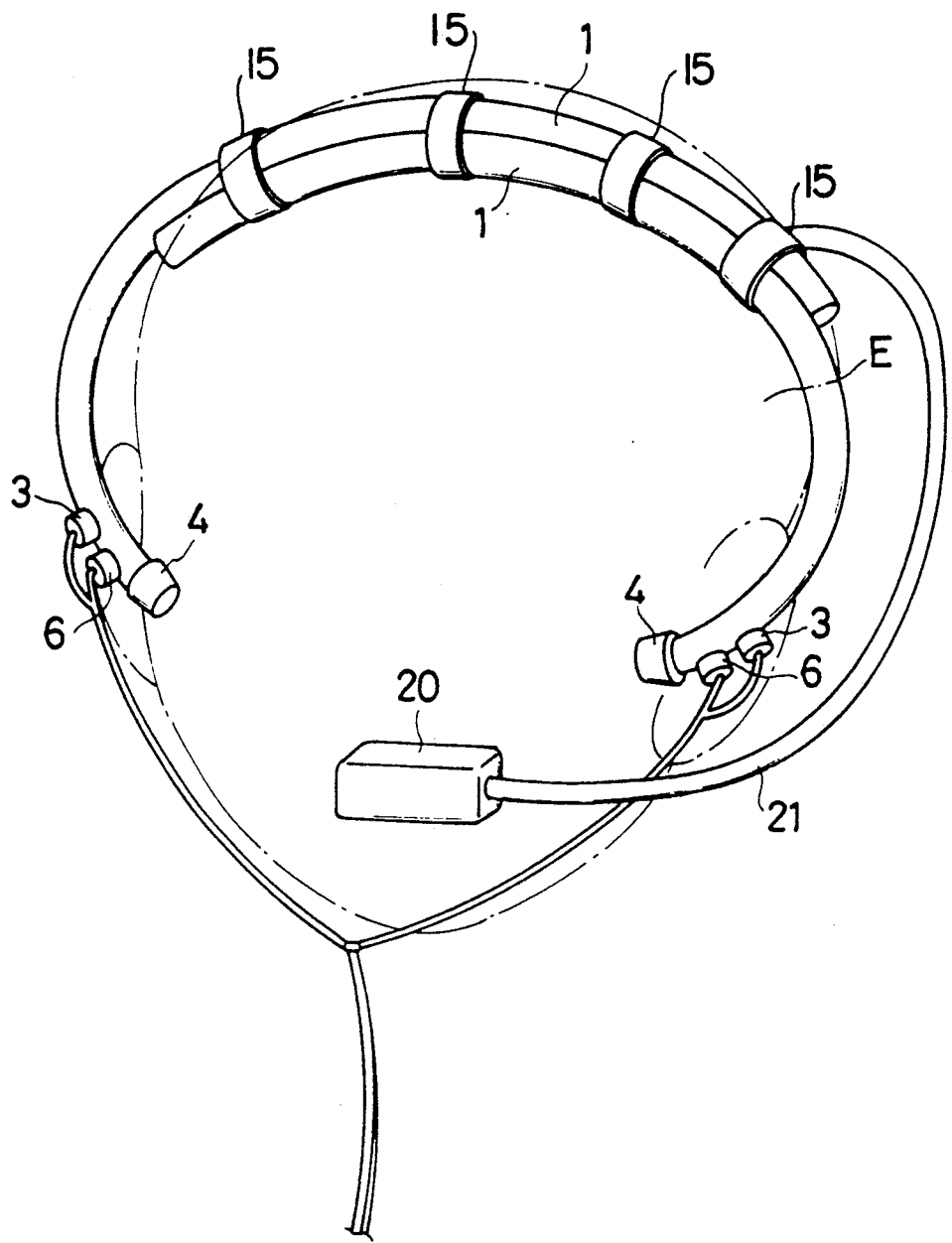
FIG. 3 is a perspective view showing the appearance of a head set to which the earphone device is applied.

FIG. 3 is a perspective view showing the appearance of a head set to which the present earphone device is applied.

In the head set shown in FIG. 3, the acoustic tube 1 is bent by such an angle that the acoustic impedance is not influenced. Two acoustic tubes 1 and 1 are linked with each other by link members 15 so that the respective mounting members 4 face the inlets of the auditory canals. One end of a bar 21 is mounted on, for example, the link member 15 and a transmitting microphone 20 is mounted on the other end of the bar 21. Two acoustic tubes 1 overhang the head E as a hair band.

If the mounting members 4 are mounted on the auricles D while the mounting members 4 of the acoustic tubes 1 are slightly opened, the mounting members 4 would be biased upon the entrances of the external auditory canals A on the both sides in such a manner that they will not press the temples of the head. The mounting members 4 are prevented from being removed from the auricles D. Comfortable wearing and clear communication can be achieved.

It is apparent from the foregoing that there is are no reflections of sounds in the tubes and no effect of localization in head occurs and external noises can be effectively reduced and a compact and light-weight earphone device can be provided. Therefore, sounds, etc. can be clearly listened to even if a high volume is not reproduced so that sounds from surroundings cannot fail to be heard. Sound distortion in the earphone unit can be reduced by the negative feedback.

If the earphone device is used as, for example, a head set, it is not necessary to cover and press the ears with headphone caps. Accordingly, fatigue due to use for a long period of time can be reduced.

The earphone device of the present invention may be, of course, used for, for example, earphone devices of compact portable headphone players and the like and handsets of telephones.

Another embodiment of the earphone device of the present invention will be described with reference to FIG. 4.

Figure 4:
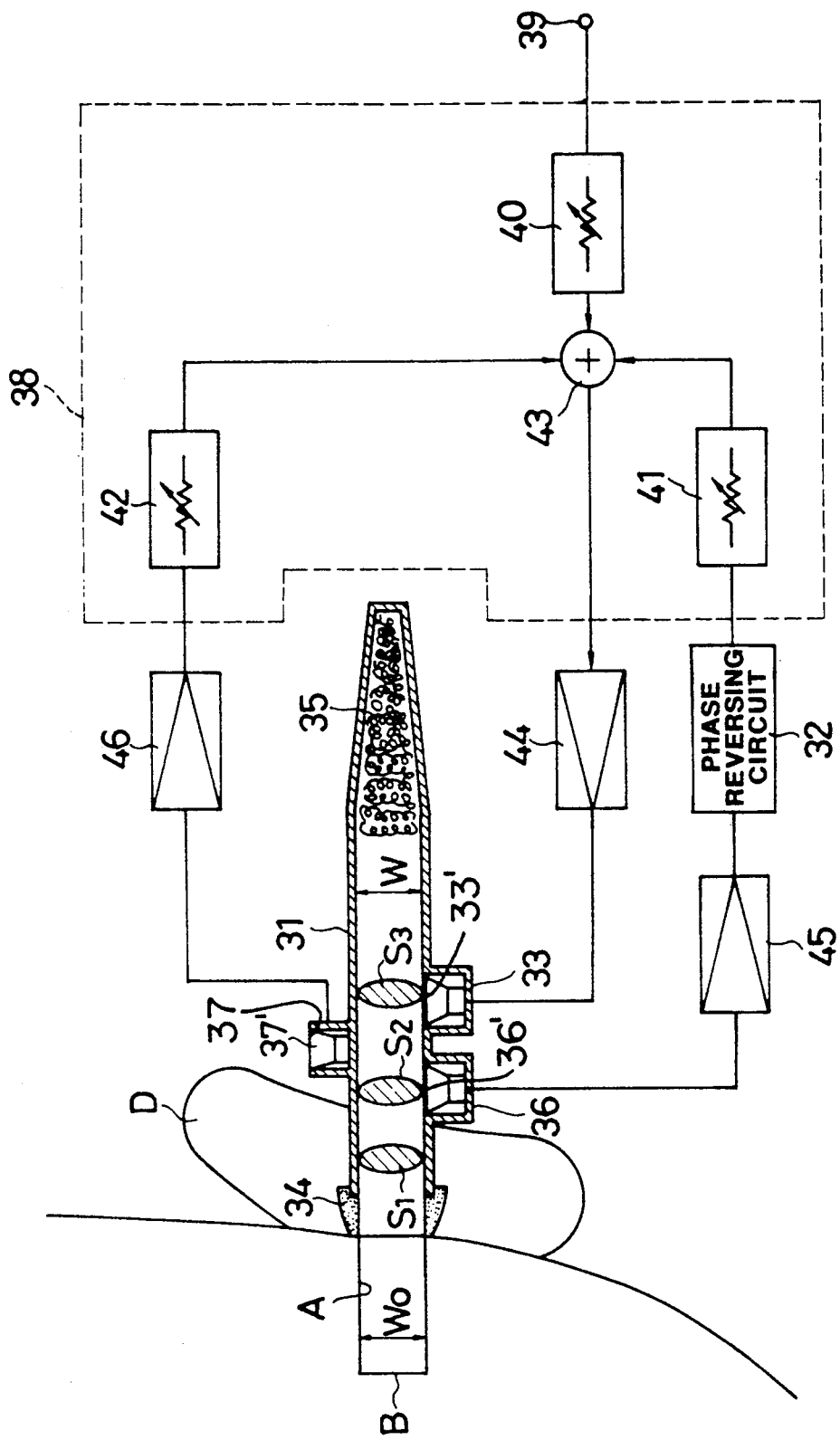
FIG. 4 is a block diagram showing another structure of the earphone device of the present invention.

In FIG. 4, the earphone device is formed so that it has an inner diameter W which is substantially identical with the inner diameter $W_0$ of the external auditory canal A.

The earphone device comprises an acoustic tube 31 having an inner diameter W which is substantially identical with the inner diameter $W_0$ of the external auditory canal A and which is provided with auricle mounting member 34 made of a material such as synthetic resin or rubber having an elasticity at one end thereof and with a sound absorbing member 35 such as felt at the other end thereof so that the other end becomes an acoustic non-reflection terminal, an earphone unit 33, an internal microphone unit 36 adjacent to the earphone unit 5 provided on the periphery of the acoustic tube 1, each having a vibration plate 33' and 36' facing inward of the tube, a phase reversing circuit 32 which reverses the phase of an audio signal in the acoustic tube 31 supplied from the internal microphone unit 36 for outputting it as a relatively fed back signal, an external microphone unit 37 disposed externally of the acoustic tube 31, which picks up external noises for outputting an external noise signal and a mixing circuit 38 which is capable of mixing the inputted audio signal such as music signal reproduced from a compact portable stereo cassette tape recorder with the negatively fed back signal and the external noise signal at a desired mixing ratio.

The mixing circuit 38 comprises a first variable gain control circuit 40 for variably changing the gain of the inputted audio signal, a second variable gain control circuit 41 for variably changing the gain of the negatively fed back signal, a third variable gain control circuit 42 for variably changing the gain of the external noise signal and an adder 43 for adding the output signals from the variable gain control circuits 40, 41 and 42.

The acoustic tube 31 forms an earphone casing. The inner diameter $W_0$ of the external auditory canal A and the sound absorbing member 35 is provided at the other end to provide the acoustic non-reflecting terminal so that the acoustic impedance of the acoustic tube 31 is made substantially identical with the impedance of the external auditory canal A. So called localization in head is thus prevented. In order to prevent a change in the acoustic impedance, the earphone unit 33 and the inner microphone unit 36 are mounted on the side of the acoustic tube 31 so that the respective vibration plates 33' and 36' are mutually parallel and the section area $S_1$ of the acoustic tube 31 is equal to the respective cross-section areas $S_2$ and $S_3$ of the mounting portions of the earphone unit 33 and the microphone unit 36.

Now, operation of the earphone device will be described.

Input audio signal such as a music signal which has been reproduced from a compact portable stereo cassette tape recorder is supplied from an input circuit 39 to an amplification circuit 44 via the first variable gain control circuit 40 and the adder 43 of the mixing circuit 38 and is amplified by the amplification circuit 44 and is supplied to the earphone unit 33.

The earphone unit 33 electro-acoustically converts the output signal from the amplification circuit 41 for providing reproduced sound.

The sound provided by the earphone unit 33 transmits to the eardrum via the external auditory canal A and is picked up by the internal microphone unit 36. The sound which is picked up by the internal microphone unit 36 is supplied as audio signal to the phase reversing circuit 32 via the amplification circuit 45.

The phase reversing circuit 32 reverses the phase of the audio signal supplied from the amplification circuit 45. The output signal from the phase reversing circuit 32 is supplied as a negatively fed back signal having a phase opposite to that of the audio signal to the adder 43 via the second variable gain control circuit 41.

On the other hand, the external microphone unit 37 picks up the external noise transmitting through the auditory canal A. The external noise signal obtained by picking up the external noise by the external microphone unit 37 is amplified by the amplification circuit 46 and is supplied to the adder 43 via the third variable gain control circuit 42.

The adder 43 adds the inputted audio signal, the negatively fed back signal, and the external noise signal with each other. The added signal is supplied to the earphone unit 33 via the amplification circuit 44.

The earphone unit 33 converts the output signals supplied from the amplification circuit 44 into an audio signal for providing sounds.

The earphone device of this embodiment is capable of controlling the mixing ratio of the input audio signal, the negatively fed back signal and the external noise signal which are added with each other in the adder 33 as mentioned above by means of the variable gain control circuits 40, 41 and 42.

That is, on normal use in which the reproduced sound of the input audio signal is desired to be listened to without being influenced by the external noise, the gain of the external noise signal is adjusted to a low value or zero by the third variable gain control circuit 42. The gains of the input audio signal and the negatively fed back signal are adjusted to desired magnitudes by the first and second variable gain control circuits 40 and 41. Therefore, excellent reproduced sound having less noises can be listened to.

Conversely, when external emergency information and human voices are desired to be listened to while listening to such reproduced sounds, the gains of the input audio signal and the negatively fed back signal are not adjusted or adjusted to low values or zero and the gain of the external noise is increased by adjusting third variable gain control circuit 42, the gain of which has been a low value or zero. The external emergency information and the human voices can be listened while the earphone device is worn, that is, without removing the earphone device from the ear.

The earphone device can be used as a so-called ear plug by turning off the first variable gain control circuit 40 so that the external noises reaching at the eardrum B are canceled by the negative feed back loop to provide a substantially silent condition. Also in this case, external sounds can be listened to while the earphone device is worn by adjusting the gain of the external noise signal by the third variable gain control circuit 42.

Adjustment of the gains of the variable gain control circuits 40, 41 and 42 can be achieved by operation of switches or knobs.

What is claimed is:

1. An earphone device characterized in that it comprises
   an acoustic tube having an inner diameter substantially identical with that of the external auditory canal and provided with an ear mounting portion at one end thereof and with an acoustic non-reflecting portion at the other end thereof;
   an external microphone unit disposed externally of said acoustic tube for converting an external sound into an electrical signal
   an earphone unit and an internal microphone unit which are mounted on the periphery of the acoustic tube in adjacent relationship with each other so that vibration plates of the units face inwardly of the tube; and
   variable ratio mixing means for mixing an input audio signal, a feedback signal obtained by negatively feeding back the signal obtained from said internal microphone unit and the electrical signal obtained from the external microphone unit with each other at a desired ratio, to form an output signal including level adjusting means for independently adjusting a level of each said input audio signal, said feedback signal, and said electrical signal from said external microphone, the output signal of said variable ratio mixing means being supplied to said earphone unit.

2. An earphone unit as defined in claim 1 in which said levels adjusting means for independently adjusting levels included in said mixing means comprises:
   a first variable gain control circuit for variably changing a gain of the input audio signal;
   a second variable gain control circuit for variably changing a gain of the feedback signal obtained by negatively feeding the signal obtained from said internal microphone unit;
   a third variable gain control circuit for variably changing a gain of the electrical signal obtained from said external microphone unit; and
   an adder for adding respective outputs from the first, second, and third variable gain control circuits.

3. An earphone device as defined in claim 1 in which said earphone unit and internal microphone unit are mounted on a side wall of said acoustic tube so that the respective vibration plates are substantially mutually parallel.

4. An earphone device as defined in claim 3 in which sides of said vibration plates of said earphone unit and internal microphone unit are flush with an inner surface of said acoustic tube.

5. An earphone device as defined in claim 4 in which said acoustic tube is of substantially the same inner diameter from said ear mounting portion to said non-reflection terminal.

* * * * *